(12) United States Patent
Skutella et al.

(10) Patent No.: US 8,445,269 B2
(45) Date of Patent: May 21, 2013

(54) METHOD FOR GENERATING PLURIPOTENT STEM CELLS

(75) Inventors: Thomas Skutella, Berlin (DE); Sabine Conrad, Tuebingen (DE); Arnulf Stenzl, Tuebingen (DE)

(73) Assignees: Thomas Skutella, Berlin (DE); Sabine Conrad, Tuebingen (DE); Arnulf Stenzl, Tuebingen (DE)

( * ) Notice: Subject to any disclaimer, the term of this patent is extended or adjusted under 35 U.S.C. 154(b) by 1023 days.

(21) Appl. No.: 12/245,596

(22) Filed: Oct. 3, 2008

(65) Prior Publication Data

US 2010/0086523 A1    Apr. 8, 2010

(51) Int. Cl.
*C12N 5/00* (2006.01)
*C12N 5/02* (2006.01)
*G01N 33/53* (2006.01)
*G01N 33/567* (2006.01)

(52) U.S. Cl.
USPC ............. 435/325; 435/7.2; 435/7.21

(58) Field of Classification Search
USPC .................. 435/325, 7.2, 7.21
See application file for complete search history.

(56) References Cited

PUBLICATIONS

Payne et al (Cell Stem Cell, Previews, p. 471-472, 2008).*
Alexander et al., Biol Chem (2002) 383:1845-1853.
Bibel et al., Nature Neurosci (2004) 7:1003-1009.
Bielby et al., Tissue Eng (2004) 10:1518-1525.
Blyszczuk et al., Int J Dev Biol (2004) 48:1095-1104.
Brinster and Avarbock, PNAS USA (1994) 91:11303-11307.
Costoya et al., Nature Genet (2004) 36:653-659.
De Rooij, PNAS USA (2006) 103:7939-7940.
Ginis et al., Dev Biol (2004) 269:360-380.
Guan et al., Nature (2006) 440:1199-1203.
Hamra et al., Dev Biol (2004) 269-393-410.
Kanatsu-Shinohara et al., Biol Reprod (2007) 76:55-62.
Kanatsu-Shinohara et al., Cell (2004) 119:1001-1012.
Kehat et al., Methods Enzymol (2003) 365:461-473.
Kubota and Brinster, Nature Clin Pract Endocrinol Metab (2006) 2:99-108.
Kubota et al., Biol Reprod (2004) 71:722-731.
Lumelsky et al., Science (2001) 292:1389-1394.
Maltsev et al., Mech Dev (1993) 44:41-50.
Matsui et al., Cell (1992) 70:841-847.
Meissner et al., Nature Biotechnol (2007) 25:1177-1181.
Meng et al., Science (2000) 287:1489-1493.
Okita et al., Nature (2007) 448:313-317.
Park et al., Nature (2008) 451:141-146.
Pollard et al., Cereb Cortex (2006) 16(Suppl 1):i112-i120.
Resnick et al., Nature (1992) 359:550-551.
Ringe et al., Med Klin (2003) 98(Suppl 2):35-40.
Schatten et al., Nature Methods (2005) 2:455-463.
Seandel et al., Nature (2007) 449:346-350.
Segev et al., Stem Cells (2004) 22:265-274.
Shamblott et al., PNAS USAS (1998) 95:13726-13731.
Shamblott et al., PNAS USAS (2001) 98:113-118.
Shinohara et al., PNAS USAS (1999) 96:5504-5509.
Stevens, Cell Differ (1984) 15:69-74.
Stukenborg et al., J Androl (2007) 29:312-329.
Turnpenny et al., Stem Cells (2006) 24:212-220.
Wernig et al., Nature (2007) 448:318-324.
Wittwer et al., Nucleic Acids Res (1989) 17:4353-4357.
Yu et al., Science (2007) 318:1917-1920.

\* cited by examiner

*Primary Examiner* — Gerald Leffers, Jr.
*Assistant Examiner* — Magdalene Sgagias
(74) *Attorney, Agent, or Firm* — Morrison & Foerster LLP

(57) ABSTRACT

The present invention relates to a method for generating pluripotent stem cells and to pluripotent stem cells generated from human testis.

10 Claims, 13 Drawing Sheets
(13 of 13 Drawing Sheet(s) Filed in Color)

|         | SC  | hES(H1) | haGSC |
|---------|-----|---------|-------|
| oct-4   | +   | +++     | +     |
| e-cad   | +   | +++     | +     |
| POU6F1  | +   | +       | ++    |
| nanog   | +   | +++     | +     |
| sox-2   | +   | +++     | +     |
| gdf3    | +   | ++      | +     |
| stat-3  | +++ | +++     | +++   |
| CD9     | +++ | +++     | +++   |
| dazl    | +++ | +       | +++   |
| klf4    | +++ | +++     | +++   |
| FGFR1   | ++  | +++     | ++    |
| otex    | ++  | +++     | +++   |
| SPAG9   | +++ | −       | −     |
| FSTL1   | ++  | +++     | +++   |
| TSPYL   | +++ | −       | −     |
| AFP     | +   | ++      | +     |
| stella  | +   | +       | +     |
| vasa    | +++ | +++     | +++   |

SEQUENCE LISTING

<160> NUMBER OF SEQ ID NOS: 12

<210> SEQ ID NO 1
<211> LENGTH: 26
<212> TYPE: DNA
<213> ORGANISM: Artificial Sequence
<220> FEATURE:
<223> OTHER INFORMATION: bisulphite primer

<400> SEQUENCE: 1

```
atattgaagt ttttagagtg tgattt                                    26

<210> SEQ ID NO 2
<211> LENGTH: 19
<212> TYPE: DNA
<213> ORGANISM: Artificial Sequence
<220> FEATURE:
<223> OTHER INFORMATION: bisulphite primer

<400> SEQUENCE: 2
ttccccttct atctcacca                                            19

<210> SEQ ID NO 3
<211> LENGTH: 24
<212> TYPE: DNA
<213> ORGANISM: Artificial Sequence
<220> FEATURE:
<223> OTHER INFORMATION: bisulphite primer

<400> SEQUENCE: 3
tttttatttt gttggatttg tgtt                                      24

<210> SEQ ID NO 4
<211> LENGTH: 18
<212> TYPE: DNA
<213> ORGANISM: Artificial Sequence
<220> FEATURE:
<223> OTHER INFORMATION: bisulphite primer

<400> SEQUENCE: 4
aacctcaatt tccctcc                                              18

<210> SEQ ID NO 5
<211> LENGTH: 19
<212> TYPE: DNA
<213> ORGANISM: Artificial Sequence
<220> FEATURE:
<223> OTHER INFORMATION: bisulphite primer

<400> SEQUENCE: 5
ggagatagtg gtttgggag                                            19

<210> SEQ ID NO 6
<211> LENGTH: 18
<212> TYPE: DNA
<213> ORGANISM: Artificial Sequence
<220> FEATURE:
<223> OTHER INFORMATION: bisulphite primer

<400> SEQUENCE: 6
accccatctt ccctaat                                              18

<210> SEQ ID NO 7
<211> LENGTH: 18
<212> TYPE: DNA
<213> ORGANISM: Artificial Sequence
<220> FEATURE:
<223> OTHER INFORMATION: bisulphite primer

<400> SEQUENCE: 7
ggtgtagggg atttaggg                                             18

<210> SEQ ID NO 8
<211> LENGTH: 22
<212> TYPE: DNA
<213> ORGANISM: Artificial Sequence
```

-continued

```
<220> FEATURE:
<223> OTHER INFORMATION: bisulphite primer

<400> SEQUENCE: 8
aaaccttttt ctacctcctt tt                                              22

<210> SEQ ID NO 9
<211> LENGTH: 21
<212> TYPE: DNA
<213> ORGANISM: Artificial Sequence
<220> FEATURE:
<223> OTHER INFORMATION: bisulphite primer

<400> SEQUENCE: 9
atggtgtttg tggaagggga a                                               21

<210> SEQ ID NO 10
<211> LENGTH: 27
<212> TYPE: DNA
<213> ORGANISM: Artificial Sequence
<220> FEATURE:
<223> OTHER INFORMATION: bisulphite primer

<400> SEQUENCE: 10
tccaaacaac taaaatatac aaaacct                                         27

<210> SEQ ID NO 11
<211> LENGTH: 28
<212> TYPE: DNA
<213> ORGANISM: Artificial Sequence
<220> FEATURE:
<223> OTHER INFORMATION: bisulphite primer

<400> SEQUENCE: 11
taatatgagg taattagttt agtttagt                                        28

<210> SEQ ID NO 12
<211> LENGTH: 27
<212> TYPE: DNA
<213> ORGANISM: Artificial Sequence
<220> FEATURE:
<223> OTHER INFORMATION: bisulphite primer

<400> SEQUENCE: 12
taatttcaaa ctctaacttc aaataat                                         27
```

METHOD FOR GENERATING PLURIPOTENT STEM CELLS

BACKGROUND OF THE INVENTION

1. Field of the Invention

The present invention relates to a method for generating pluripotent stem cells, a method of autologous cell transplantation with a human being, and to pluripotent stem cells generated from human testis.

2. Related Prior Art

Stem cells are cells found in most, if not all, multi-cellular organisms. They are characterized by the ability to renew themselves through mitotic cell division and differentiating into a diverse range of specialized cell types. As stem cells can be grown and transformed into specialized cells with characteristics consistent with cells of various tissues such as muscles or nerves through cell culture, their use in medical therapies has been proposed. In particular, embryonic cell lines, autologous embryonic stem cells generated through therapeutic cloning, and highly plastic adult stem cells from the umbilical cord blood or bone marrow are touted as promising candidates.

The ability to derive pluripotent stem cells from the adult human testis has important implications for biotechnology and regenerative medicine. Although these cells are unipotently restricted to the generation of gametes in the course of normal development[2,3], several lines of evidence suggest that under certain circumstances, cells of the germ line have the ability to give rise to cells that are pluripotent[4-6]. The term of pluripotency is differently defined in research with mouse and human stem cells. The NIH and the ISSCR guidelines and criteria for human pluripotency include teratoma formation in addition to microarray assays for transcription factors and other gene activity associated with pluripotency. Teratomas, which are tumors containing different kinds of cells and tissues from all three germ layers at various stages of maturation, occur almost exclusively in the gonads[7]. Furthermore, primordial germ cells (PGCs) give rise to pluripotent cells when cultured under appropriate conditions[4,8]. PGCs have differentiation properties similar to those of embryonic stem (ES) cells isolated from the inner cell mass[9]. Recently the successful establishment of germline stem cells from neonatal mouse testis was reported[5]. In addition, one study[6] successfully generated mouse adult germline stem cells (GSCs) with pluripotency from spermatogonial stem cells from adult mouse testis. As in the experiments reported previously[5], these cells were able to differentiate into derivatives of all germ layers in vitro, generated teratomas in immunodeficient mice and, when injected into an early blastocyst, contributed to the development of various organs. Similar results with GPR125+ germline progenitor cells have been reported by another study[10].

Since there are considerable differences between stem cells from mice and human stem cells[9] the pluripotent stem cells of mice as generated by Guan et al.[6] are limited in their clinical applications in human. Therefore, there is an ongoing need to provide a reliable method for generating human adult pluripotent stem cells which can be used in clinical applications, e.g. stem cell therapies, autologous transplantations etc.

SUMMARY OF THE INVENTION

Against this background the object underlying the invention is to provide a method for generating human adult pluripotent stem cells having an expression profile comparable to such of human embryonic stem cells (hESCs) representing an alternative to human induced pluripotent stem cells (hiPSCs).

This object is achieved by the provision of a method for generating human adult pluripotent stem cells, comprising the following steps (1) providing cells isolated from human testicular parenchyma, (2) cultivating said cells in the presence of at least one stem cell growth factor, (3) isolating a first subpopulation of said cells expressing at least one stem cell surface marker, (4) contacting said first subpopulation with collagen, (5) isolating a second subpopulation from said first subpopulation consisting of cells not binding to said collagen ($Col_{NB}$ cells), (6) contacting said $Col_{NB}$ cells with laminin, (7) isolating a third subpopulation from said $Col_{NB}$ cells consisting of cells binding to said laminin ($Lam_B$ cells), (8) cultivating said $Lam_B$ cells in the presence of leukemia inhibitory factor (LIF) for obtaining pluripotent stem cells.

The object underlying the invention is herewith fully achieved. Especially such a method is provided which avoids ethical problems since no intervention in a human embryo is required.

The inventors have demonstrated that the obtained human pluripotent stem cells, also referred to as human adult germ line stem cells (haGSCs) are highly stable and could be cultivated over a long period of time (over 40 passages and more), and remain highly proliferative. The inventors have also demonstrated that by the method according to the invention the generation of pluripotent stem cells is fully reproducible.

It is preferred if said at least one stem cell growth factor in step (2) of the method according to the invention is a member of the family of glial cell line-derived neurotropic factor (GDNF).

This measure has the advantage that such a growth factor is provided which maintain the cells isolated from human testicular parenchyma in an undifferentiated state.

In the method according to the invention it is preferred if said at least one stem cell surface marker in step (3) is selected from the group consisting of: CD49f ($\alpha_6$-integrin), CD90 (Thy-1), GDNF receptor alpha 1 (GDNFR-$\alpha$1), and CD133. It is highly preferred if said at least one stem cell surface marker is CD49f ($\alpha_6$-integrin).

This measure has the advantage that such a marker is used which ensures spermatogonial stem cell enrichment.

According a preferred embodiment, the isolation in step (3) is realized by performing magnetic activated cell separation (MACS) using beads comprising molecules capable of binding to said at least one stem cell surface marker.

This measure has the advantage that a well established and reliable separation method is used which ensures the enrichment of spermatogonial stem cells.

According to a preferred embodiment of the invention, step (8) comprises step (8.1) by which cells with a normal karyotype 46 XY) are selected to obtain said pluripotent stem cells.

This measure has the advantage that only such cells are used as pluripotent stem cells which on a genetic level give no course for concern in view of a medical application.

It is preferred, if step (8) comprises step (8.2) by which cells are selected capable of inducing teratomas to obtain said pluripotent stem cells.

The induction of teratomas, e.g. in vivo after injection of the cells in immunodeficient mice, demonstrates that the generated stem cells are in fact pluripotent. No other test would be sufficient for unambiguously proving the pluripotency of the generated stem cells.

It is furthermore preferred, if step (8) comprises step (8.3) by which cells are collected capable of differentiating into cells of all three germ layers to obtain said pluripotent stem cells.

The measure provides additional certainty that the generated cells have in fact pluripotent properties. Pluripotency is often defined as the capability of stem cells to differentiate into any of the three germ layers: endoderm (interior stomach lining, gastrointestinal tract, the lungs), mesoderm (muscle, bone, blood, urogenital), or ectoderm (epidermal tissues and nervous system).

It is also preferred if step (8) of the method according to the invention comprises step (8.4) by which cells are selected with activated transcriptional regulatory network to obtain said pluripotent stem cells.

By this measure another criteria of pluripotency established by the NIH and the ISSCR guidelines is fulfilled, that gives additional certainty that the generated cells have in fact pluripotent properties. "Activated transcriptional regulatory network" means that the cells have a specific transcriptional state, e.g. demethylated Oct4 and Nanog promoters.

It shall be understood that steps (8.1) to (8.4) might not necessarily be performed in the sequential order of (8.1), (8.2) ... (8.4), but also in another order, i.e. a renumbering of the steps is possible. Furthermore, the steps can be performed independently of each other, e.g. step (8.2) does not depend on step (8.1), step (8.3) does not depend on steps (8.2) or (8.1), and step (8.4) does not depend on steps (8.3), (8.2) or (8.1), and so on.

According to a preferred embodiment of the method according to the invention, in step (8) the cultivated cells were passaged approximately every 14 days.

This measure has the advantage that only such cells are obtained which have constant doubling rates and are highly stable in cell culture.

It is preferred if said cultivation in step (8) occurs in basic medium on a gelatine coated cell carrier.

This measure has the advantage that an environment is provided which ensures a proper cultivation of the generated cells. As basic medium any stem cell medium can be used, whereby it is preferred if such a medium is used that comprises the following ingredients: DMEM high glucose, 15% FCS (Biochrom), 1% non-essential amino acids (NEAA), 1% L-glutamine and 0.05 mM β-mercaptoethanol (Gibco) with $10^3$ units ml$^{-1}$ leukemia inhibitory factor (LIF, human, Chemicon))[5].

In another embodiment of the method according to the invention, said cultivating in step (2) occurs in knockout medium on an uncoated cell carrier.

This measure has the advantage that such an environment is provided which ensures a proper cultivation of the cells isolated from the human testicular parenchyma. Knockout culture medium can e.g. obtain from Invitrogen, catalogue number 10829018, referred to as GIBCO™ Knockout™ T-MEM.

According to a preferred embodiment, step (1) of the method according to the invention comprises the following steps: (1.1) mechanical disruption and/or enzymatic dissociation of human testicular parenchyma to obtain a digest, and (1.2) filtering said digest to obtain single cells isolated from said human testicular parenchyma.

This measure has the advantage that well-established methods are used ensuring the obtainment of a single cell suspension consisting of cells from human testicular parenchyma.

Another subject matter of the present invention is a method of autologous cell transplantation with a human being, comprising the following steps: (1) isolating cells from the testicular parenchyma of said human being, (2) performing steps (2) to (8) of the method for generating human adult pluripotent stem cells according to the invention, to obtain human adult pluripotent stem cells, and (3) transplantation of said human adult pluripotent stem cells into said human being.

The features, preferred embodiments and advantages described in relation with the method for generating pluripotent stem cells according to the invention, apply to the method of autologous cell transplantation with a human being according to the invention mutatis mutandis.

Against this background another subject matter of the present invention is a pluripotent stem cell generated from human testis, preferably from human testicular parenchyma, which is preferably generated by the method according to the invention.

The features and advantages described in relation with the method for generating pluripotent stem cells according to the invention, apply to the pluripotent stem cell according to the invention correspondingly.

It goes without saying that the afore-mentioned features and the features to be described in the following cannot only be used in the identified combinations but also in different combinations or in isolated form, without departing the scope of the present invention.

The present invention is now described in more detail by means of embodiments which are of pure illustrative character and do not limit the scope of the invention. Reference is made to the enclosed Figures:

BRIEF DESCRIPTION OF THE DRAWINGS

The patent or application file contains at least one drawing executed in color. Copies of this patent or patent application publication with color drawings will be provided by the Office upon request and payment of the necessary fee.

a-i, Immunohistochemistry with the germ and stem cell markers NANOG, SSEA4, OCT4, e-cadherin, TSPYL2, DAZL, CD133 and the selection marker CD49f in spermatogonial cells. Co-expression of CD49f and VASA in spermatogonial cells is shown. Nuclei were stained with 4,6-diamidino-2-phenylindole (DAPI) and magnifications (original magnification 340) show nuclear or cytoplasmic staining.

Figure 1A:
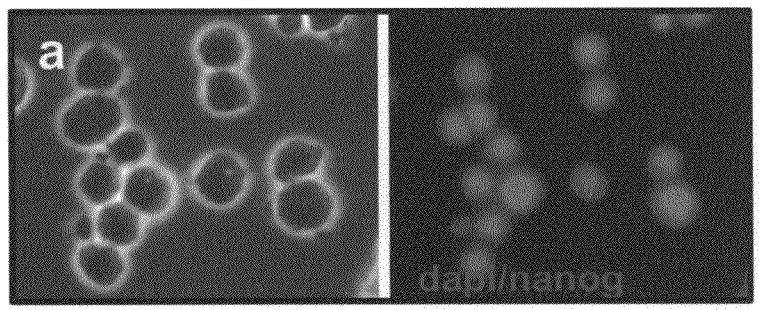
FIG. 1 Selection of spermatogonial cells from adult human testis.
Figure 1B:
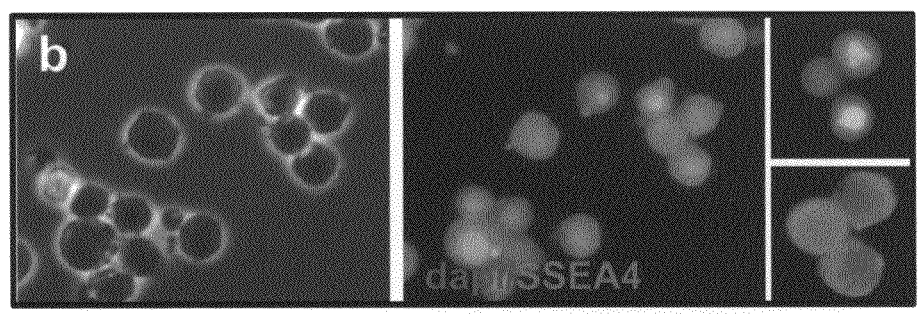
Figure 1C:
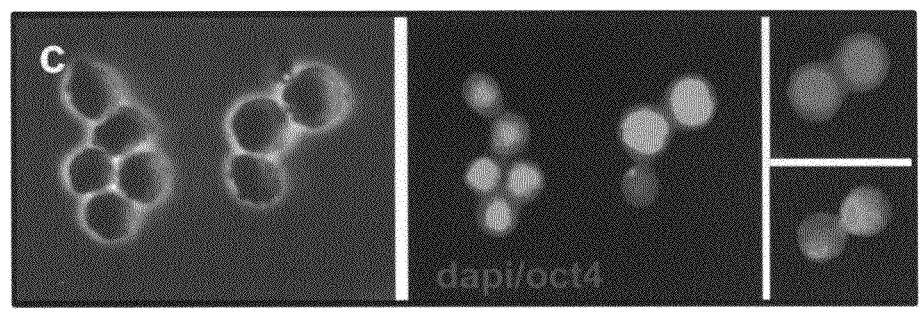
Figure 1D:
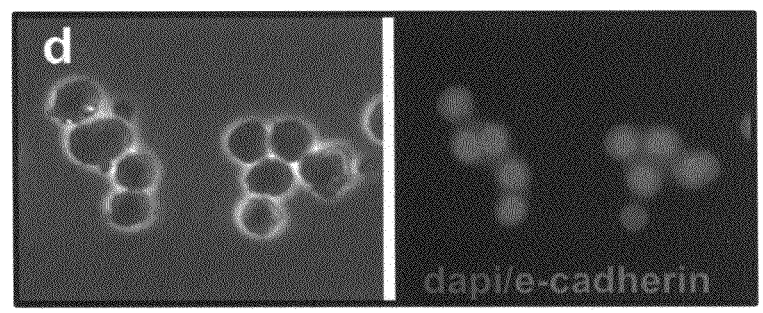
Figure 1E:
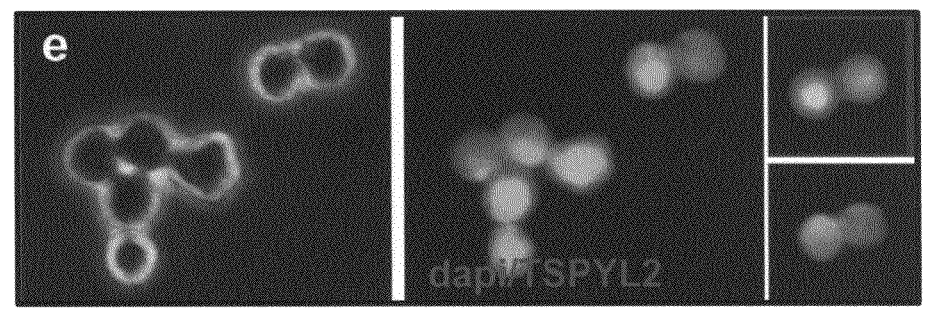
Figure 1F:
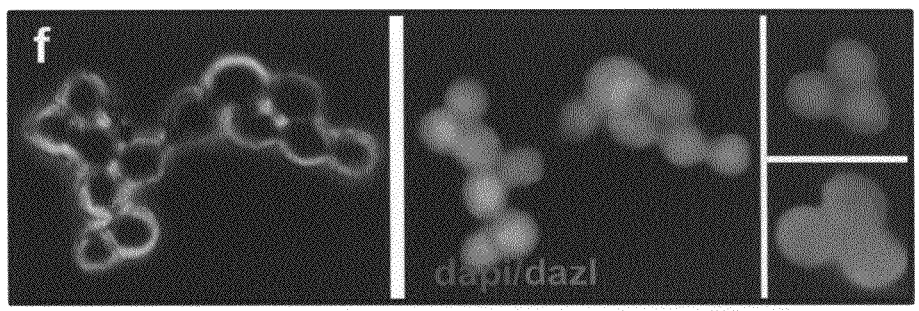
Figure 1G:
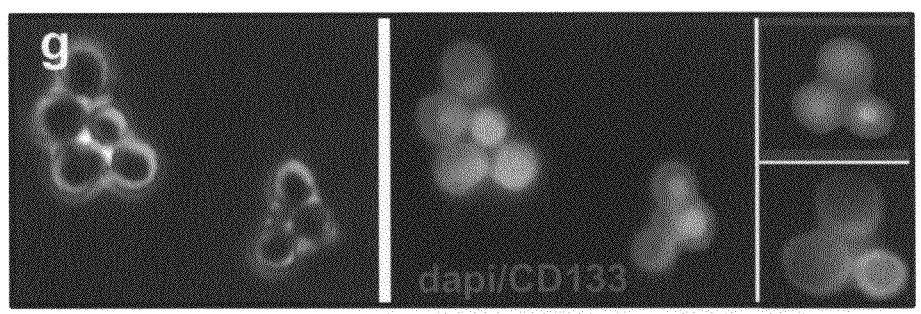
Figure 1H:
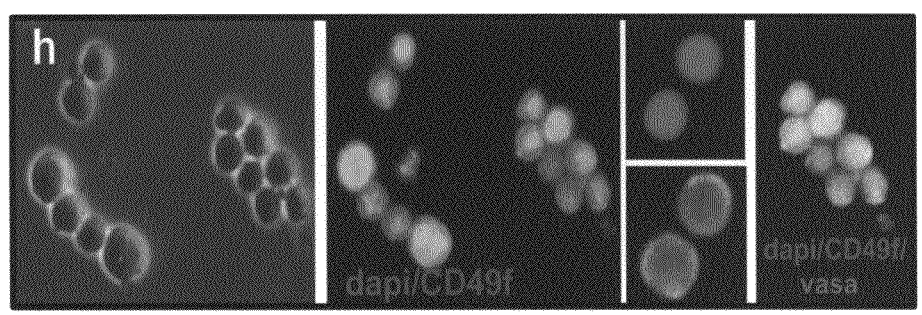
Figure 1I:
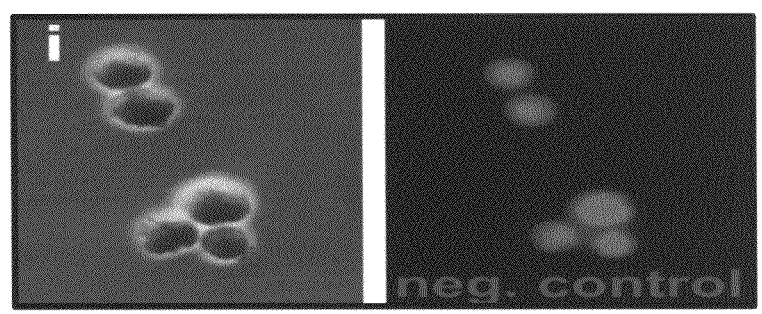
Figures 1, 2, 2A, 3, 4:
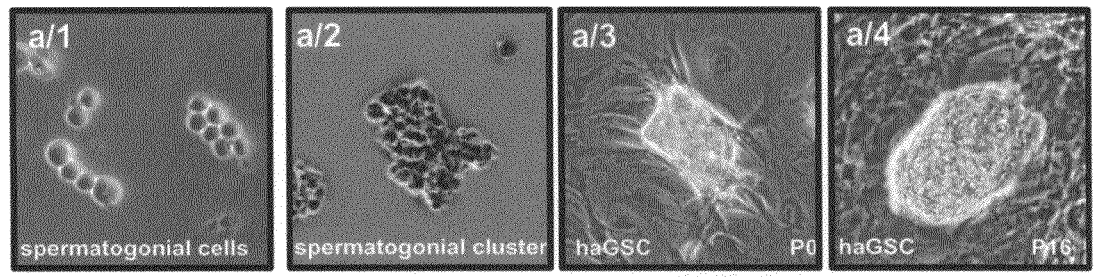

FIG. 2 Generation of human adult GSCs from spermatogonial cells.

a, Panel 1 shows colonies of spermatogonial cells on laminin (Lam$_B$ cells). Panel 2 shows a proliferating spermatogonial cell colony (panel 2). Panel 3 shows an early human adult GSC cluster (haGSC; panel 3). A human adult GSC cluster at higher passage (P16) (panel 4) and an overview of typical human adult GSC clusters (far right panel) is also shown. b, RT-PCR of LIF receptor complex in human adult GSCs cultured under GDNF/LIF or LIF alone from lower (P1) and higher (P7) passage in comparison to FGF2-cultivated H1 cells. A 1-kilobase DNA ladder is shown. c, Western blot analysis of human adult GSCs under LIF from passage 3, 7 and 14, H1 cells and neural differentiated human adult GSCs. d, Percentage of formed clusters after plating spermatogonial cells for 14 days under different growth factors over a further cultivation time period of 42 days expressed. e, Comparison of the doubling times of human ES cells (H1) and human adult GSCs from passage 3 and 36 over a 120-h period. Error bars in d and e show standard deviations (n=3).

FIG. 3 Characterization of the human adult GSCs in comparison to normal testis tissue.

a, Comparison of stem cell, testis and spermatogonial markers in normal human testis, spermatogonial cells and human adult GSCs. b, Alkaline phosphatase staining of human adult GSC and human ES dissociated clusters as cytospin and HEK293 cells as negative control. Alkaline phosphatase was strongly positive in human adult GSC and human ES cell clusters. c, Immunostaining of human adult GSC clusters with NANOG, e-cadherin, OCT4, CD133, SSEA4, VASA, CD49f and DAZL. Columns from left to right: left, bright field; middle, double staining of stem cell marker with DAPI with areas of magnification; right, magnification of boxed area showing nuclear or cytoplasmic staining.

FIG. 4 Molecular profiling and epigenetics of human adult GSCs.

a, PCA diagrams comparing spermatogonial cells (SC), human adult GSCs and human ES (hES) populations and all biological replicates (upper panel). Expression profile of germ- and stem-cell-specific transcripts revealed a similar expression pattern of human ES cells (green) and human adult GSCs (brown) (lower panel). Human spermatogonial cells (blue) differed significantly from the other samples. PC1, first principal component; PC2, second principal component. For all groups n=3. b, Stem cell and testis expression profiles in all three cell types. The expression rate of genes is shown in different signs and colours: 2/yellow, not expressed; 1/light green, low; 11/blue, moderate; 111/red, high. c, Comparison of gene expression between human ES cells and human adult GSCs by real-time PCR. Amplified genes are shown in different colours. The mRNA levels were normalized to GAPDH and error bars show standard deviations (n=3). d, Average amplificate methylation of POU5F1 and NANOG promoter genes with sample grouping by cell type. Colour codes indicate 0% (yellow) over 50% (green) to 100% (dark blue) methylation. The y axis shows amplificate location at individual CpG positions. The x axis shows samples that are grouped by cell type and passage (LP, passage 3; HP, passage 7).

Figures 2, 2A, 3, 4, 5:
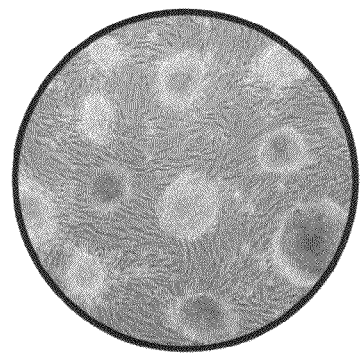

FIG. 5 Human adult GSC-derived human teratoma formation after injection into an immunodeficient mouse.

Complete section (low-resolution image; mosaic scan with X40 original magnification) of the gross anatomy of the subcutaneous tumour formation is shown at the top; higher-magnification images (X63 original magnification) of boxed areas are shown below. Panel 1 shows formation of ectodermal structures (stratified keratinizing epithelium developed). Panel 2 shows mesodermal structures from human adult GSCs with cartilage and smooth muscle. Panel 3 shows development of endodermal structures with pseudostratified columnar epithelium (top left), glandular structures (top right) and gut-like simple columnar epithelium (bottom left). HE, haematoxylin and eosin stain.

DETAILED DESCRIPTION OF EMBODIMENTS

1. Material and Methods
1.1 Cell culture of human adult GSCs.

The experiments with human material were approved by the local ethics council (University Clinic Tübingen). Informed consent was obtained from all the human subjects.

The obtained human testis tissues were mechanically disrupted and enzymatically dissociated with 0.5 g ml$^{-1}$ collagenase type VI (Sigma) and 0.25 g ml$^{-1}$ dispase II (Roche) in HBSS buffer with Ca$^{2+}$ and Mg$^{2+}$ (PAA) for 30 min at 37° C. Then the digest was pelleted at 1,000 r.p.m., washed twice with knockout culture medium (Gibco) with 20% ES cell qualified FBS and 1% L-glutamine and filtered through a 40 µm mesh to obtain a single cell suspension. Cells were plated into 10 cm$^2$ culture dishes at 2×10$^6$ cells per cm$^2$ containing medium with 4 ng ml$^{-1}$ GDNF (Sigma) and incubated at 32.5° C., 5% CO$_2$ for 96 h. Medium was removed after 96h and testis cell cultures were gently washed with 4 ml of DMEM high glucose (PAA) and once with 4 ml of PBS. Bound germ cells were harvested from monolayers of adherent somatic cells by repeated pipetting with 4 ml of DMEM. The pooled suspension was pelleted at 1,000 r.p.m., suspended in 10 ml DMEM and filtered through a 40-mm mesh. For further purification MACS separation (Miltenyi) with biotinylated CD49f (α$_6$ integrin; BioLegend) and anti-biotin beads was applied[5,15,16]. After MACS separation, cells from five 10-cm dishes were transferred to a 10-cm plastic dish coated with collagen 1 (5 µg cm$^{-2}$, Becton Dickinson) and incubated at 32.5° C. for 4 h in basic medium (DMEM high glucose, 15% FCS (Biochrom), 1% non-essential amino acids (NEAA), 1% L-glutamine and 0.05 mM β-mercaptoethanol (Gibco) with 10$^3$ units ml$^{-1}$ leukaemia inhibitory factor (LIF, human, Chemicon))[5]. Cells that did not bind to collagen I dishes (Col$_{NB}$ cells) were harvested and pelleted at 1,000 r.p.m. The Col$_{NB}$ cells were suspended in basic medium and plated at 0.5–1×10$^6$ cells per ml per well in 12-well plates pre-coated with laminin (4.4 µg cm$^{-2}$, Sigma). The plated Col$_{NB}$ cells were incubated for 45 min at 32.5° C. and unbound cells (Col$_{NB}$/Lam$_{NB}$ cells) were removed from bound cells (Lam$_B$ cells) by pipetting and discarded. The Lam$_B$ cells were rinsed twice with 1 ml DMEM. The Lam$_B$ cells then were harvested by gentle pipetting and cultured in basic medium on 0.1% gelatine-coated 48-well plates. Under these conditions the spermatogonial cells proliferated first and aggregated, and then human adult GSC clusters were formed. We only used a few (500) purely isolated spermatogonial cells to generate human adult GSC cultures from the patients in 48-well plates. Generally the cells were passaged mechanically every 14 days. Clusters were manually isolated and cut into pieces and plated on gelatine-coated dishes. Only cell cultures with a normal karyotype (46, XY in all of the examined metaphase spreads) in low (P3) and high (P36) passages were used.

For purposes of comparison all the experiments were also performed in parallel with the human ES cell line H1 in the laboratory of J. Hescheler (Cologne, Germany). The H1 cells were cultured in knockout DMEM (Invitrogen), 20% knockout serum replacer (Invitrogen), 1 mM L-glutamine (Invitrogen), 1% NEAA (Invitrogen), 0.1 mM β-mercaptoethanol (Gibco), 1% penicillin/streptomycin (Gibco) and 4 ng ml$^{-1}$ FGF2 (Peprotech) on CF1-inactivated feeders on 0.1% gelatine-coated dishes and passaged mechanically every 6-7 days. Colonies were cut manually into pieces, counted and distributed on new feeder-coated dishes (~1.34×10$^4$ cells cm$^{-2}$)[26].

1.2. Testing of Different Culture Conditions.

Different medium combinations were tested with spermatogonial cells cultured on 0.1% gelatine-coated dishes or on different coatings. To this end spermatogonial cells were plated for 14 days and the formed clusters observed for another 42 days under 8 different conditions. (1) Basic medium directly from the beginning of culture with LIF (10$^3$ units ml$^{-1}$); (2) condition 1 but with FGF2 (4 ng ml$^{-1}$); (3) knockout medium with GDNF (4 ng ml$^{-1}$) for the first 4 days followed by basic medium with LIF; (4) knockout medium with GDNF; (5) condition 4 but with FGF2 (4 ng ml$^{-1}$); (6) knockout medium or basic medium without GDNF, FGF2 or LIF; (7) condition 1 or 3 on a combination of laminin, fibronectin and poly-L-ornithine; (8) condition 1 or 3 on matrigel.

1.3 Quantification of the Doubling Time of Human Adult GSCs and Human ES Cells.

For this experiment 3×10$^5$ cells per plate from three different passages of human adult GSCs and human ES cells were seeded in 6-well plates. Clusters were cut from human adult GSCs and human ES cultures, digested, counted and replated every 24 h over a time period of 120 h.

1.4 Differentiation of Human Adult GSCs and Human ES Cells.

The isolated cells were transposed into specific established culture media to initiate differentiation into all three germ layers. We used specific protocols for myogenic[27,28], osteogenic[29,30], pancreatic[31-33] and neural[34,35] differentiation of human ES cells. All the differentiation protocols were repeated at least three times under each set of conditions using mechanically isolated clusters from human adult GSCs and human ES (H1) cells.

1.5 Alkaline Phosphatase Staining of Cytospins of Human Adult GSCs and Human ES Cells.

For staining, clusters were mechanically isolated and dissociated with trypsin EDTA for 5 min at 37° C. After blocking with 10% FCS and washing with PBS, 1×10$^6$ cells were resuspended in 0.5 ml PBS and centrifuged as cytospins for 4 min at 1,100 r.p.m. Then the spins were fixed with 2% paraformaldehyde for 5 min and stained with NBT/BCIP. HEK293 cells were used as controls.

1.6 Immunohistochemistry.

To characterize human spermatogonia, human adult GSCs and the differentiation into derivatives of the three primary germ layers, we examined the expression of a panel of cell-specific proteins for spermatogonial cells, human ES cells and markers of myogenic, osteogenic, pancreatic and neural differentiated cells.

1.7 Antibodies and Staining.

The following primary antibodies were used: mouse monoclonal biotinylated anti-CD49f (BioLegend), rabbit polyclonal anti-OCT4 (Abcam), mouse monoclonal anti-SSEA4 (Chemicon), rabbit polyclonal anti-NANOG (Biozol), mouse monoclonal anti-e-cadherin (R&D Systems), goat polyclonal anti-human VASA (R&D Systems), rat monoclonal anti-Stella (R&D Systems), rabbit polyclonal anti-p27 (Abcam), mouse monoclonal anti-SOX17 (R&D Systems), goat polyclonal anti-FOXA2 (R&D Systems), rat monoclonal anti-CXCR4 (BD Pharmingen), mouse monoclonal anti-GSC (Abnova), mouse monoclonal anti-human c-peptide (BioVendor), rabbit polyclonal anti-insulin (Santa Cruz), rabbit polyclonal anti-human glucagon (Dako), mouse monoclonal anti-α-actinin (Sigma), rabbit polyclonal anti-smooth muscle actin (Spring Bioscience), rabbit polyclonal anti-glia fibrillary acidic protein (GFAP) (Dako), mouse monoclonal anti-b-tubulin-III (TUJ-1) (Convance), mouse monoclonal anti-neurofilament (Dako), mouse monoclonal anti-glutamate (Sigma), rabbit polyclonal anti-GABA (Sigma), rabbit polyclonal anti-cytokeratin (Dako), and mouse monoclonal anti-α-fetoprotein (Chemicon). Alexa Fluor-488-conjugated goat anti-mouse IgG, Alexa Fluor-488-conjugated goat anti-rabbit IgG, Alexa Fluor-488-conjugated goat anti-rat IgG (Molecular Probes), Cy3-conjugated goat anti-mouse IgG, Cy-conjugated goat anti-rabbit IgG and Cy-conjugated goat anti-rat IgG (Dianova) were used as secondary antibodies with co-staining with DAPI. In addition biotinylated swine anti-rabbit, biotinylated rabbit anti-mouse and biotinylated goat anti-rat (Dako) with ABC complex (streptavidin/horseradish peroxidase) and DAB staining with haemalaun or DAPI as co-staining were used. For negative controls, isotype mouse, goat, rat or rabbit IgGs were used. Alkaline phosphatase staining was carried out using NBT/BCIP substrate (Roche).

1.8 Western Blot Analysis.

Clusters of human adult GSCs, H1, HEK293 and human adult GSC neural differentiated cells were lysed in RIPA buffer and sonicated. The probes were denatured in sample buffer, analysed in a 12% SDS-PAGE and after blotting stained with the specific antibodies for NANOG, OCT4, SSEA4, e-cadherin, STAT3 (Santa Cruz) and pSTAT3 (Santa Cruz). For negative control HEK293 or blocking peptides for STAT3 and pSTAT3 were used (data not shown).

1.9 RT-PCR Analysis.

Tissues and cells were homogenized in lysis buffer and total RNA was prepared using the RNeasy Mini Kit (Qiagen). cDNA for human ES cells was obtained from the stem cell line H1. mRNA was reverse transcribed using Oligo (dT)23 primer (Sigma) and SupercriptII-transcriptase (Invitrogen). cDNA was amplified.

1.10. Real-time PCR Analysis.

Steady state mRNA levels were enumerated by quantitative RT-PCR (qRT-PCR, LightCycler, Roche) as described[36]. The qRT-PCR was performed as touch-down PCR in 35 cycle[37]. Quantification of GAPDH and serial dilutions of recombinant standard DNAs served as controls in each PCR. Transcript amounts are presented as copy numbers normalized to GAPDH and the recombinant standards. Analysis of melting curves confirmed product quality after each PCR.

1.11 Flow Cytometric Analysis.

The following unconjugated and conjugated antibodies were used for FACS analysis: mouse monoclonal anti-CD34 (BD Pharmingen), anti-CD44-FITC (Becton Dickinson), mouse monoclonal anti-CD45 (BD Pharmingen), anti-CD90-APC (BD-Pharmingen), mouse monoclonal anti-CD105 (Ancell), anti-CD117-FITC (Chemicon), mouse monoclonal anti-CD133 (University Clinic of Tübingen), rat monoclonal anti-SSEA3 (R&D Systems), anti-SSEA4-APC (BD Pharmingen), mouse monoclonal TRA 1-60, mouse monoclonal TRA 1-81 (Santa Cruz), e-cadherin (R&D Systems) and the intracellular antibodies for OCT4, NANOG (Abcam) and pSTAT3 (Santa Cruz). For intracellular staining the cells were fixed with 2% para-formaldehyde and permeabilized with 0.1% Triton X-100 before labelling. At least 10,000 events were acquired on a FACSCanto II cytometer (Becton Dickinson) using the FACS express software for analysis.

1.12 Electron Microscopy.

After embedding in Epon (Fluka), semithin sections (1 mm) were prepared and from them ultrathin sections (100 nm). Semithin sections were stained with toluidine blue and embedded in epoxy resin for ultrathin sectioning in electron microscopy. Digital micrographs were taken with a Zeiss Axioskop microscope.

1.13 Methylation Assay.

The methylation assay was conducted by Epigenomics (Berlin). Briefly, after quality control was performed for 18 DNA samples from spermatogonial cells (directly after matrix selection), human adult GSCs (from lower and higher passages), human ES cell line H1 and from human ES cells (obtained from S. Minger), the genomic DNA was treated with sodium bisulphite. PCR primers were designed for the regions of interest in the specified genes. Two regions of interest in the IGF2R and H19 genes were studied. The first region in the H19 gene is 550 bp upstream of the Vega H19-012 transcript within a CpG-rich region and at the 59 UTR of the annotated Ensembl transcript NR_002196.1 within a CpG-rich region. It contains the TSS of the reference sequence. The second region of interest in the IGF2R gene is 273 bp upstream of the annotated Ensembl transcript MPRI_HUMAN near a CpG island and within the imprinting controlling region 1 (ICR1) and a CpG island in intron 2. This region is known as imprinting controlling region 2 (ICR2). The following regions of interest in POU5F1 (annotated OCT4 orthologous human gene) and NANOG genes were studied: POU5F1 gene (reference sequence: NM_002701) AMP1000122 located at the 59 UTR of the annotated Ensembl transcript POUF 1_HUMAN (ENST00000259915), 150 bp upstream of the TSS. NANOG gene (reference sequence: NM_024865) AMP1000123 located at the 59 UTR of the annotated Ensembl transcript NANOG_HUMAN (ENST00000229307), 25 bp upstream of the TSS. The following bisulphite primers were used for PCR and for sequencing: H19 (5' UTR) 5'-ATATTGAAGTTTTTAGAG-TGTGATTT-3' (SEQ ID NO:1) and 5'-TTCCCCTTCTATCTCACCA-3' (SEQ ID NO:2); IGF2R (TSS) 5'-TTTTTATTTTGTTGGATTTGTGTT-3' (SEQ ID NO:3) and 5'-AACCTCAATTTCCCCTCC-3' (SEQ ID NO:4); H19 (TSS) 5'-GGAGATAGTGGTTTGGGAG-3' (SEQ ID NO:5) and 5'-ACCCCATCTTCCCC-TAAT-3' (SEQ ID NO:6); IGF2R (intron 2) 5'-GGTGTAGGGGATT-TAGGG-3' (SEQ ID NO:7) and 5'-AAAC-CTTTTTCTAC-CTCCTTTT-3' (SEQ ID NO:8); POU5F1 5'-ATGGT-GTTTGTGGAAGGGG-AA-3' (SEQ ID NO:9) and 5'-TCCAAACAACTAAAATATACAAAACCT-3' (SEQ ID NO:10); NANOG 5'-TAATATGAGGTAATTAGTTTAGTT-TAGT-3' (SEQ ID NO:11) and 5'-TAATTTCAAACTCTAACTTCAAATAAT-3' (SEQ ID NO:12).

In addition, DNA from peripheral blood lymphocytes (sample name Pro) and artificially hyper- and hypomethylated DNA samples (sample names Up and Down, respectively) were included as controls. Bisulphite-converted DNA was amplified using these primers and the PCR products were directly sequenced. Methylation results were quantified using Epigenomics' proprietary software ESME, which allows the quantification of DNA methylation at single CpG positions. The statistical significance of the differential methylation observed between sample groups was tested using Wilcoxon's rank sum test.

1.14 Microarray Analysis.

Total RNA was isolated from n=3 independent cell preparations of spermatogonial cells (directly after matrix selection), human adult GSCs (from lower and higher passages), human ES cell line H1 and from human ES cells (obtained from S. Minger) using the RNeasy Mini Kit (Qiagen) followed by an amplification step with the MessageAmp aRNA Kit (Ambion). Samples were analysed independently. Gene expression analyses were performed using the Human U133+ 2.0 Genome oligonucleotide array (Affymetrix) and all transcript intensities were GC-RMA normalized and analysed with a t-test using the ArrayAssist 4.0 software (Stratagene). Transcripts with more than a twofold estimated difference in expression were further considered for evaluation. For stringent multiple testing correction we used the Bonferroni-Holm procedure. In addition, we applied the web-based interactome network entry tool developed by Ingenuity Systems.

1.15 Insulin ELISA.

Quantitative insulin determination by ELISA was performed as described previously[33]. The supernatants were analysed with the insulin ELISA kit (YK060, Cosmo, Ltd) and the ultrasensitive c-peptide ELISA kit (Mercodia).

1.16 Transplantation Procedures.

For all implantation and transplantation experiments the mice were anaesthetized with an isoflurane inhalation system. The experimental protocols were approved by the local governmental council for animal care (Regierungspräsidium Tübingen) and were conducted according to the German law for the care and use of laboratory animals.

1.17 Transplantation of Human Adult GSCs in Nude Mice.

Approximately $1 \times 10^7$ human adult GSCs were injected intramuscularly or subcutaneously in the neck region of adult nude mice. After 6-8 weeks the transplants and developed tumour regions were dissected, fixed in 4% paraformaldehyde and embedded in paraffin. For the evaluation of transplant differentiation, teratoma formation was defined as being when tissue representatives of at least all three germ layers were detected in the implants. Assessment of graft histology and function was performed by in situ hybridization, histochemistry with haemalaun and immunohistochemical methods.

1.18 Microsatellite Profile Analysis of DNA from all Cells Used in this Study.

Genomic DNA was extracted from the cell culture samples using the QIAamp MicroDNA Mini Kit (Qiagen). A selected set of DNA microsatellite markers was sent to the local Microarray Facility (Tubingen, Germany) for analysis. DNA samples were PCR amplified using a multiplex microsatellite marker panel (PowerPlex16, Promega). Amplicons were separated by capillary electrophoresis (ABI310, AppliedBiosystems) and respective marker alleles were called using the PowerTyper macro in comparison with a co-analysed allelic ladder (Promega).

2. Results 2.1 Generation of Pluripotent Human Adult GSCs

The inventors used in total 22 different human testicular parenchymas to generate human adult GSCs. The obtained tissues were mechanically and enzymatically dissociated and filtered to obtain a single-cell suspension containing cells of varying sizes and shapes. In a next step the single cells were cultured for 4 days in uncoated dishes with knockout culture medium with glia-drived neutrotrophic (GDNF), a growth factor essential for the self-renewing division of spermatogonial stem cells[11], or culture directly in leukaemia inhibitory factor (LIF; ref. 12)-supplemented medium (basic medium), which is sufficient to maintain mouse ES cells or embryonic germ cells[13,14] in an undifferentiated state. Under these conditions most of the single testis cells attached to the culture plate. For the pre-selection of spermatogonial cells with magnetic-activated cell separation (MACS) the inventors used CD49f ($\alpha_6$ integrin)[15,16], a marker selected by the inventors from the different tested surface antigens. By using other antibodies like CD90 (Thy-1) or GDNFR-$\alpha$1, which have been described in the literature for mouse spermatogonial stem cell enrichment (see for example[17,18]), or CD133 (a marker for human ES and precursor cells) the inventors achieved comparable but not better selection (data not shown). An important tool to gain a highly pure spermatogonial cell population is the subsequent matrix selection procedure with collagen and laminin[19] to extract spermatogonial cells for further cultivation with basic medium and LIF to generate human adult GSCs. With this procedure the inventors were able to obtain a pure population of spermatogonial cells (VASA$^+$vimentin$^-$) and completely deplete somatic cells (VASA$^+$vimentin$^-$) (FIG. 1). After this selection and purification, colonies of spermatogonial cells appeared (FIG. 2a, panel 1) and increased in size (FIG. 2a, panel 2). After 10-15 days, these colonies changed their morphology (FIG. 2a, panel 3), became multilayered and clearly demarcated colonies with boundaries appeared (FIG. 2a, panel 4). These colonies continued to increase in number and size (FIG. 2a, far right panel). Functional proof is provided by the fact that the negative fraction of somatic cells (VASA⁻vimentin⁺) did not form stem cell colonies under LIF supplementation and were negative for stem cells markers, and even more importantly did not form any teratomas. In contrast, even after long-term cultivation the VASA¹vimentin²human adult GSC colonies behaved more like human ES cells in their molecular profile and differentiation capacity, and formation of teratomas.

Figures 3A, 3B:
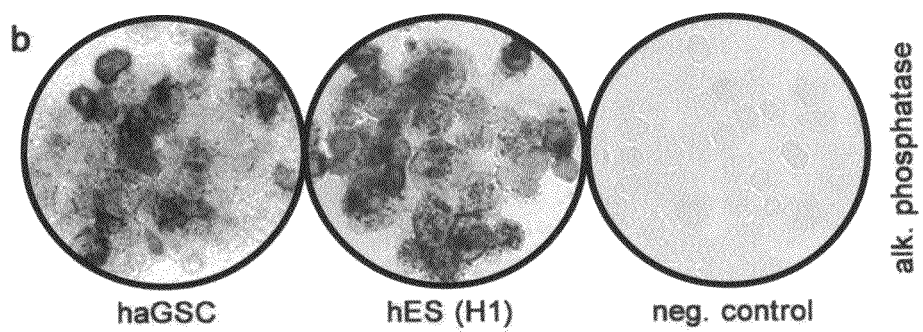
Figures 1, 3C:
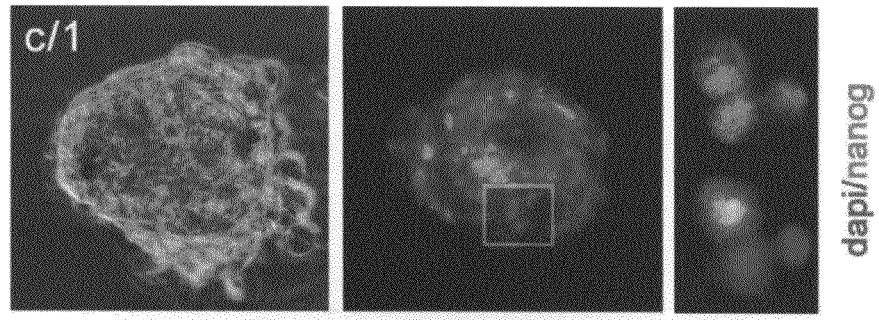
Figures 2, 3C:
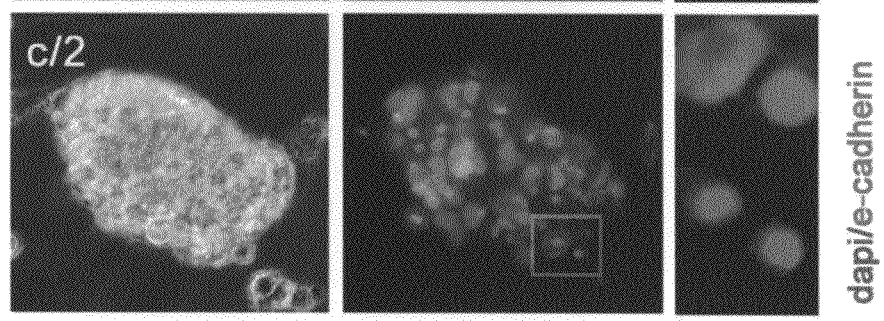
Figures 3, 3C:
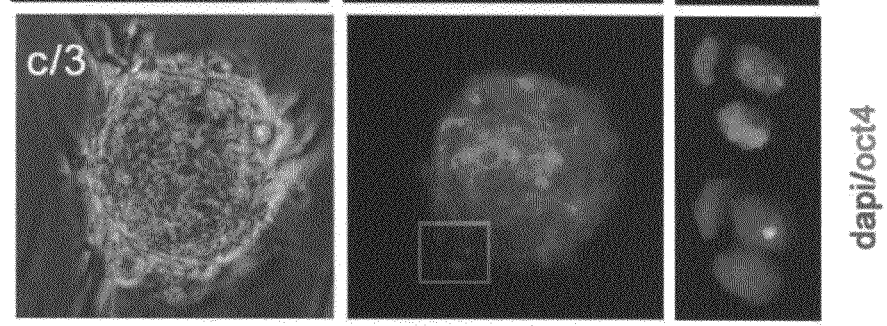
Figures 3, 3C, 4:
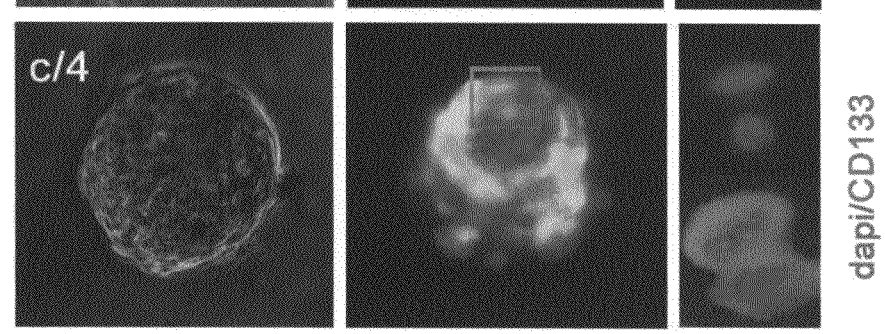
Figures 3, 3C, 4, 5, 6, 7, 8:
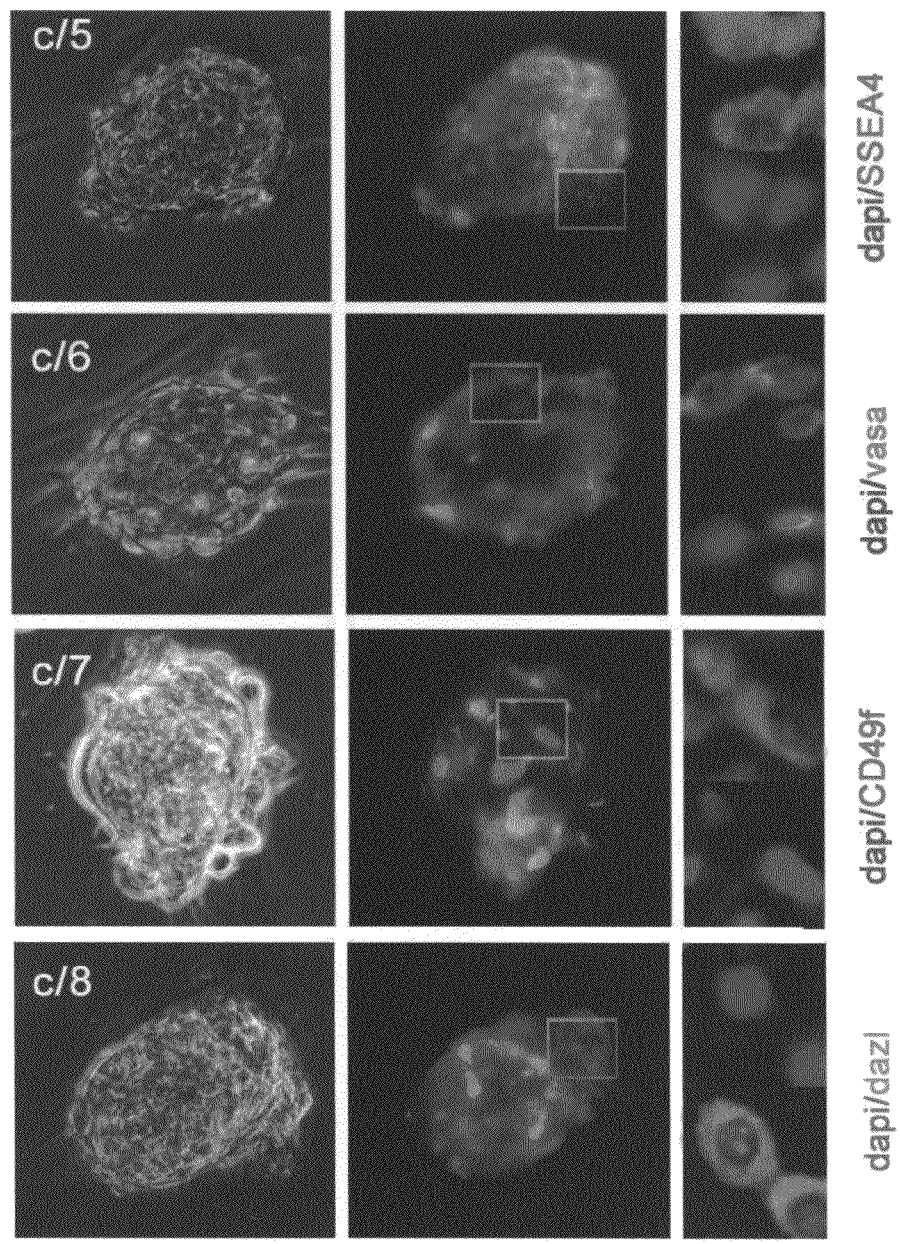

Electron microscopy of purified spermatogonial cells showed typical morphological characteristics of spermatogonia. A more detailed immunohistochemical characterization revealed that these cells were positive for VASA, SSEA4, OCT4, TSPYL2, DAZL, CD133 and CD49f, but negative for NANOG and e-cadherin and the somatic marker vimentin (FIGS. 1, 3a).

Generally the cells were passaged once or twice 3 to 4 weeks after initiation of the culture. After passaging the multilayered colonies reappeared with constant doubling times up to high passages (over 40 and higher).

Figure 2B:
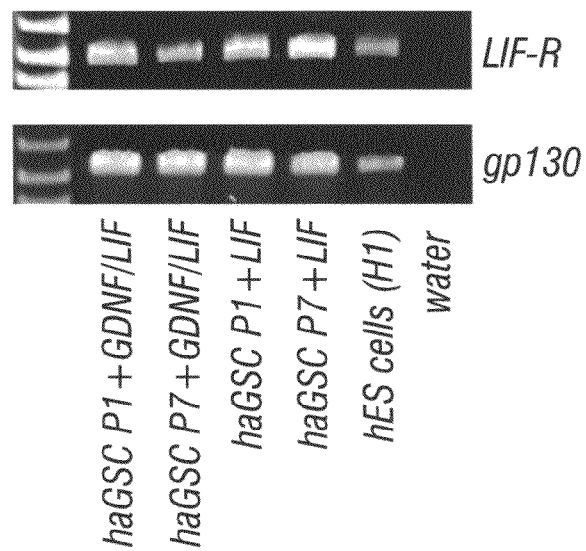
Figure 2C:
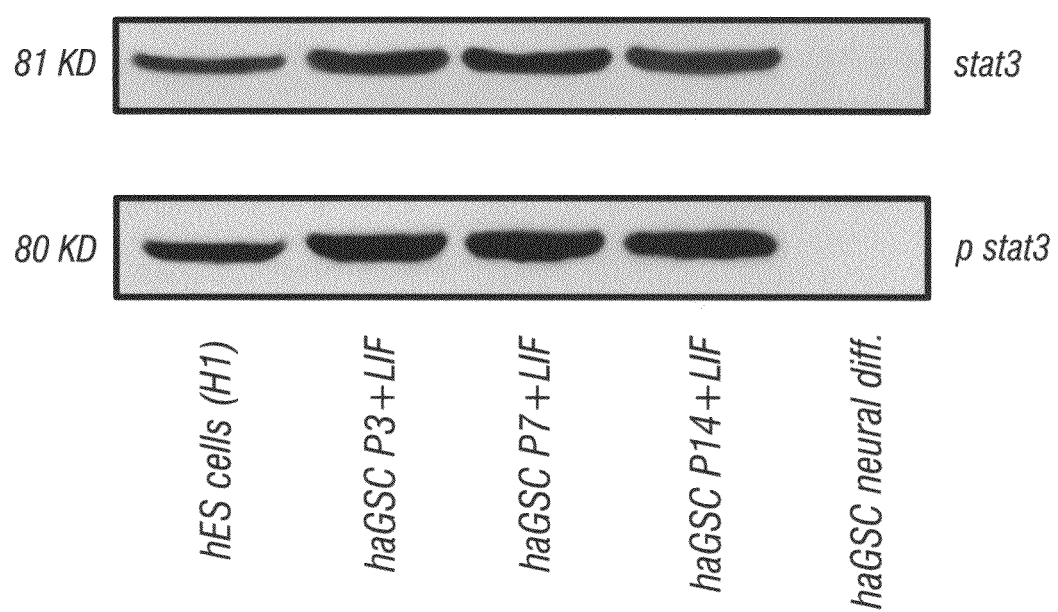
Figure 2D:
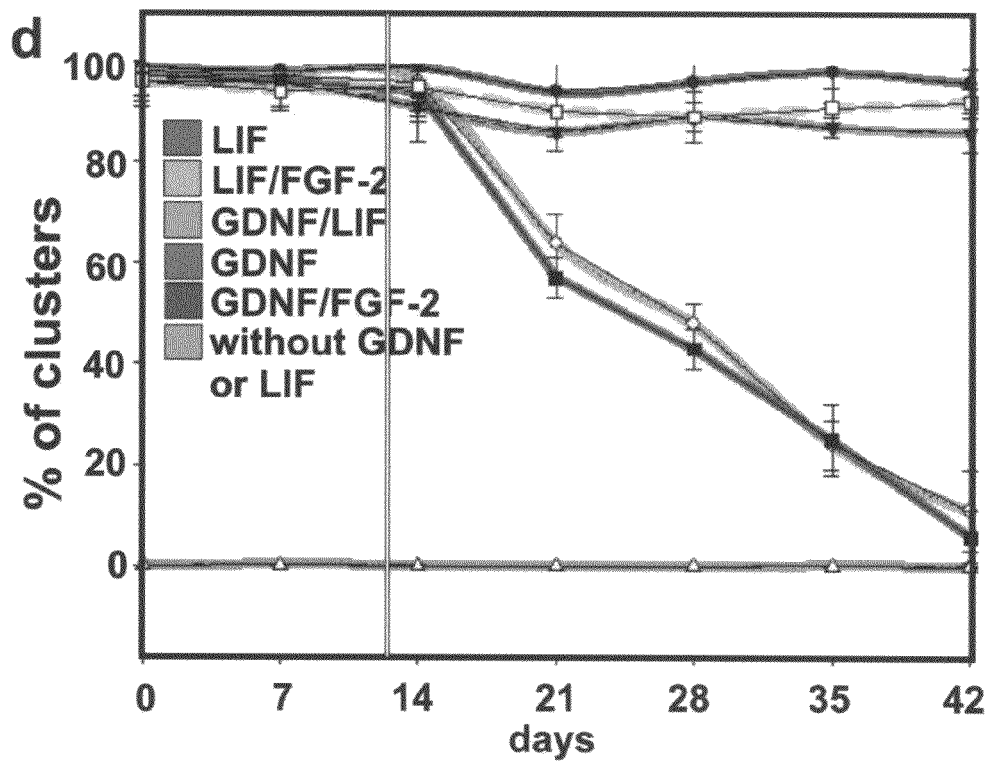

The inventors also tested different medium conditions for their ability to induce the generation of human adult GSCs (FIG. 2d). To do this, the inventors plated spermatogonial cells for 14 days under different conditions and observed the formed colonies over another 42-day period (FIG. 2d). Without supplementation with GDNF and LIF no clusters were formed at all. In contrast, both LIF alone and GDNF followed by LIF resulted in a constant rate of cluster formation over 42 days; with GDNF alone and GDNF with FGF2 clusters were formed, but the proliferation rate declined after 14 days. The combination of LIF and FGF2 did not improve human adult GSC culture.

To prove the dependence of the inventor's stem cells on LIF supplementation, LIF and gp130 receptors were detected in human adult GSCs with polymerase chain reaction with reverse transcription (RT-PCR; FIG. 2b). Furthermore, western blot analysis of STAT3 and phosphorylated STAT3 showed that this pathway is activated in human adult GSCs. These observations imply that LIF has a role in human adult GSC propagation.

Figure 2E:
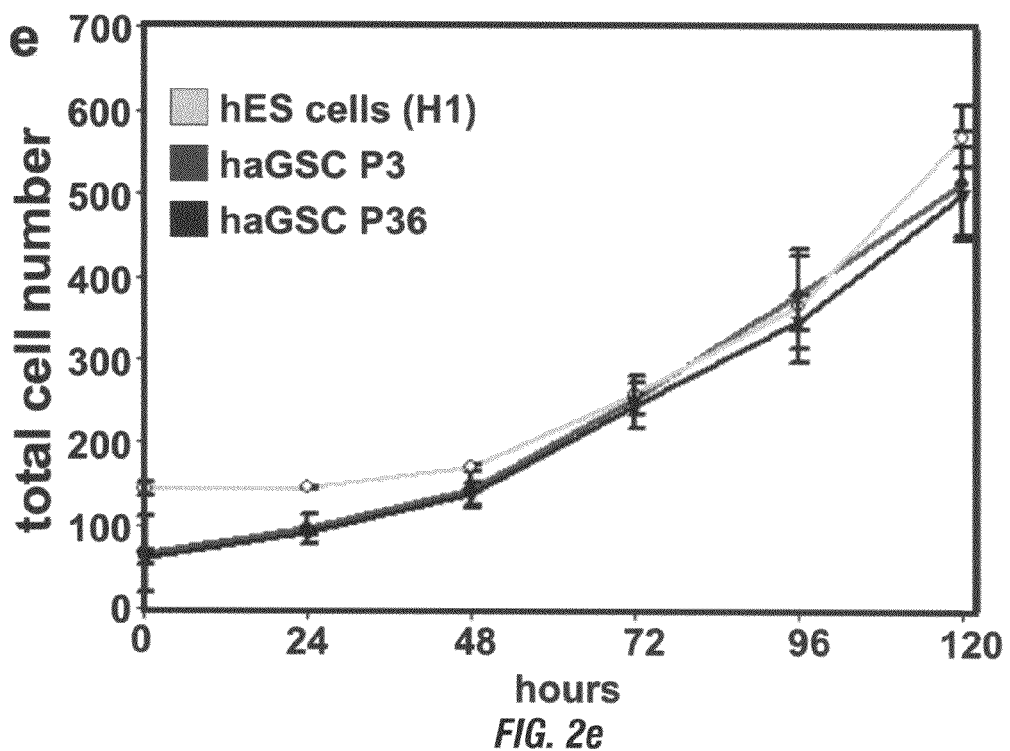

To test the expansion rate the inventors compared the doubling times of different passages of human adult GSCs to those of human ES (H1) cells, counting the total cell numbers at 24-h intervals for approximately 120 h. The doubling times of human adult GSCs were very similar to those of human ES cells across lower and higher passages (FIG. 2e).

2.2 Human Adult GSC Characterization

For a more detailed examination of the human adult GSC colonies the inventors performed immunohistochemical analysis and compared them to selected spermatogonial cells and normal adult human testis (FIGS. 1, 3a, c). In normal adult human testis tissue, spermatogonia were positive for CD133, SSEA4, VASA, DAZL, TSPYL2 and CD49f, but negative for NANOG, e-cadherin, OCT4 and Stella. The same staining pattern was shown by the purified human spermatogonial cells, except that the transcription factor OCT4 started to be expressed (FIGS. 1 and 3a). Only morphologically typical Sertoli cells in the human testis stained positive for p27. Alkaline phosphatase was highly expressed in cytospins of undifferentiated human adult GSCs and human ES cells, in contrast to differentiated HEK293 control cells (FIG. 3b). In contrast, the generated human adult GSC colonies were strongly positive for NANOG, e-cadherin, OCT4, CD133 and SSEA4 (ES cell markers) (FIG. 3a, c) and negative for p27 (a Sertoli cell marker) and Stella (a PGC marker) (FIG. 3a, panel 1). The human adult GSCs were also strongly positive for VASA, CD49f and DAZL (FIG. 3a, c).

Fluorescence-activated cell sorting (FACS) analysis provided quantitative information on the proportion of human adult GSC cells under LIF-supplemented culture conditions expressing particular surface markers in comparison to H1. These human ES cells typically expressed CD90, CD133, NANOG, e-cadherin, OCT4, SSEA4, SSEA3, TRA 1-60, TRA 1-81 and phosphorylated STAT3, and were negative for CD34, CD45, CD105 and CD117. In comparison, the expression profile of human adult GSCs was very similar. The only difference observed was the expression of CD117 (c-Kit).

RT-PCR analysis was carried out with cDNA from adult human testis, spermatogonial cells, human ES (H1) and human adult GSCs (under two different medium conditions) from lower and higher passages. In adult human testis and spermatogonial cells, stem cell and spermatogonial cell markers (OCT4, n-cadherin, STAT3, SOX2, AFP, Stella, DAZL, VASA) were expressed, but not the markers NANOG, e-cadherin and GDF3. In contrast, human adult GSCs expressed all of these markers. Under LIF supplementation, the cultured human adult GSCs started to express the ES cell factors NANOG, e-cadherin and GDF3 as well, markers which were not expressed in the adult human testis and spermatogonial cells.

Figure 4A:
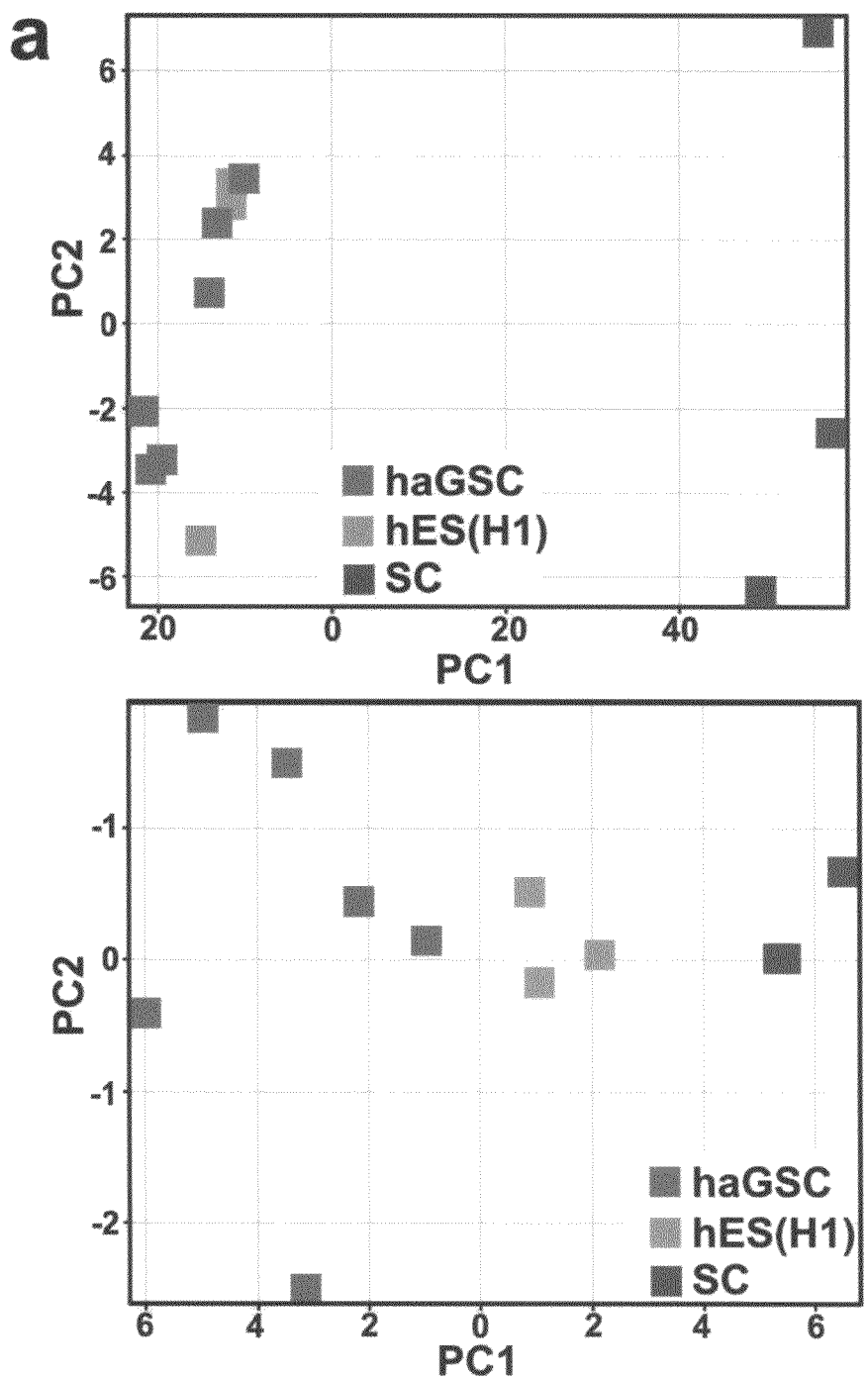
Figure 4C:
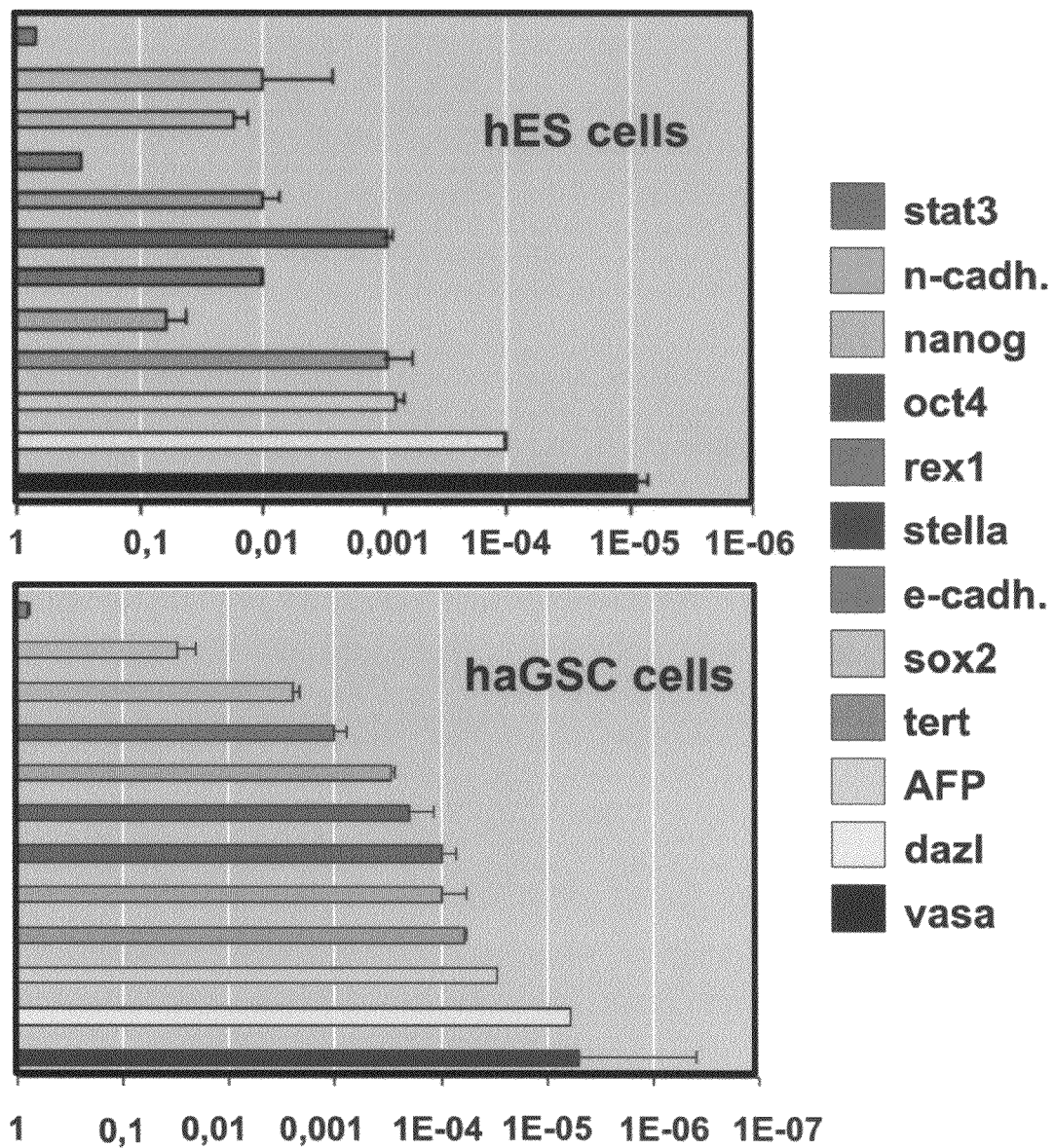

Western blot analysis also showed that NANOG, e-cadherin, OCT4 and SSEA4 were expressed by human adult GSCs under LIF supplementation (Supplementary FIG. 4c). These results suggest that human adult GSCs respond to culture conditions and acquire more human ES cell properties.

The expression of spermatogonial and human ES cell markers is maintained even in higher passages. This indicates that the cultured human adult GSCs have a stable, stem-cell-like phenotype.

In a next step the inventors investigated and compared the global gene expression patterns of spermatogonial cells, human ES cells and human adult GSCs by microarray analysis (FIG. 4a). After principal component analysis (PCA) of germ- and stem-cell-specific transcripts the inventors found very similar gene expression profiles of human adult GSCs and human ES cells with minor differences. In contrast, the expression profile of spermatogonial cells changed during development to human adult GSCs. The gene products in which expression was found to differ significantly between human ES cells and human adult GSCs are involved in tissue, organ and embryonic development, cell cycle, cellular assembly and organization, and cellular growth and proliferation.

Among the genes most significantly upregulated in human adult GSCs in comparison to human ES cells are members of the WNT-b-catenin and TGF-b signalling pathways.

FIG. 4b shows selected examples of stem cell and testis marker expression profiles from the molecular analysis comparing human adult GSCs, human ES cells and spermatogonial cells. Expression analysis of human adult GSCs compared with human ES cells and spermatogonial cells revealed high levels of STAT3, CD9, KLF4, OTEX and VASA in both human adult GSCs and human ES cells. POU6F1 and DAZL expression was stronger in human adult GSCs. OCT4, e-cadherin, NANOG, SOX2 and GDF3 expression was stronger in human ES cells. Minimal expression of the germ cell marker Stella was seen in all cell types. SPAG9 and TSPYL2 were more highly expressed in spermatogonial cells, which clearly indicates their germline origin.

The real-time PCR analysis demonstrated that human ES cells and human adult GSCs both express a similar transcription profile of markers used to characterize human ES cells (FIG. 4c). The alignment of genes showed few differences and the human adult GSCs differed from human ES cells only in expression potency. Taken together, the examinations of transcription in human ES and human adult GSCs provide evidence of a network of genes characteristic of pluripotent stem cells.

To determine whether the maintenance of genomic imprinting was compromised the inventors assessed the methylation pattern of the imprinted genes H19 and IGF2R with DNA isolated from human ES cells (H1, P48), spermatogonial cells (P0) and human adult GSCs from four different normal patients obtained from two passages (LP, P1-P3; HP, P7-P36). Spermatogonial cells showed a typical methylation pattern known for male germ cells, with hypermethylation of the maternal differentially methylated region (DMR) located at the 5' untranslated region (UTR) of the H19 gene and no methylation of the paternal DMR imprinting control region surrounding the transcriptional start site (TSS) of the IGF2R gene. The same methylation was observed for undifferentiated Hi cells which have a normal XY karyotype.

In general, both spermatogonial and H1 cells were hypermethylated (>90%) at the 5' UTR of the H19 gene and showed about 75% methylation in human adult GSCs. The amplificate located surrounding the TSS of the IGF2R gene was unmethylated (<5%) in all samples studied. The inventors did not find differential methylation among the different human adult GSC groups in any of the analysed regions when samples were grouped according to cluster or when samples of lower and higher passages of human adult GSCs were compared (data not shown). These observations indicate that human adult GSCs change their methylation pattern in the DMR of imprinting sites and display a pattern similar to that of mouse spermatogonial stem cells as shown previously[5].

In addition, when analyzing other sites of expected differential methylation, H1 cells showed higher methylation (approximately 75%) than spermatogonial cells and human adult GSCs (approximately 50%) in the amplificate surrounding the TSS of the H19 gene. In turn, the imprinting controlling region (ICR) within intron 2 of the IGF2R gene was differentially methylated in spermatogonial cells, H1 and human adult GSCs (approximately 50%, 100% and 75%, respectively).

Figure 4D:
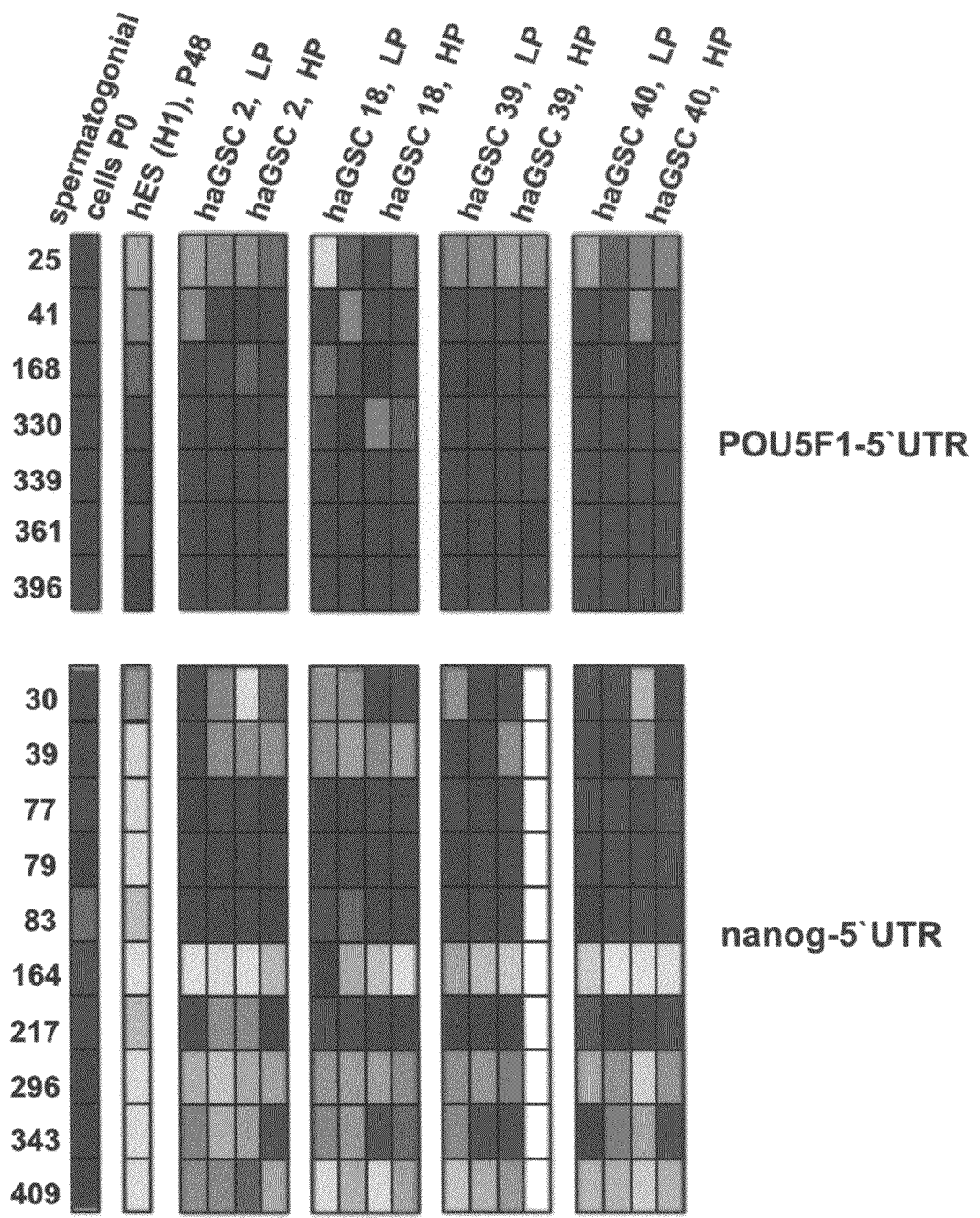
Figure 5:
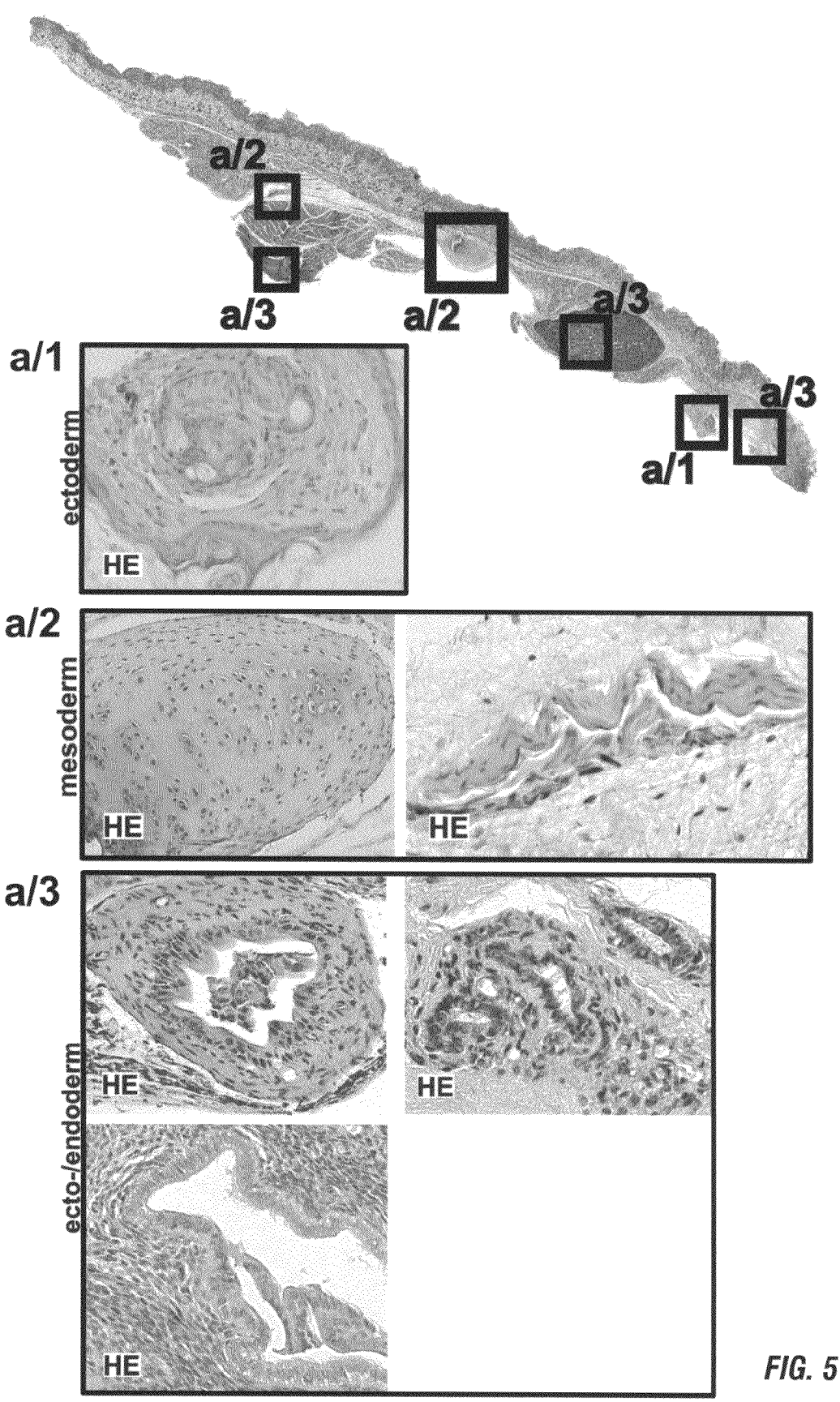

Next the inventors investigated DNA methylation levels on the putative human OCT4 (also called POU5F1) and NANOG promoters. As shown in FIG. 4d, when DNA methylation results were grouped by cell type the inventors found regions of differential methylation. Amplificates located at the 5' UTR of the OCT4 and NANOG genes showed cell-type-specific DNA methylation of spermatogonial cells, H1 cells and human adult GSCs. Whereas spermatogonial cells were hypermethylated (100%) at the 5' UTR of the OCT4 gene, Hi cells (60%) and human adult GSCs (50%) were less methylated at CpG genomic position 25-168, but were hypermethylated (100%) between positions 330 and 396. In addition, spermatogonial cells were again hypermethylated (approximately 90%) at the 5' UTR of the NANOG gene, whereas HI cells displayed low methylation (approximately 20%) and human adult GSCs also showed clearly lower (approximately 40%) methylation than spermatogonial cells. These results indicate that the epigenetic state of the OCT4 and NANOG promoter genes was reprogrammed to a more human ES-like state when human adult GSCs were generated from spermatogonial cells.

Human adult GSCs were also examined for their pluripotency in forming teratomas in vivo after injection in immunodeficient mice. The human adult GSC cells from eight different patients were injected (n=4 sets of cells per patient) and gave rise to typical teratoma structures in nude mice by 6 to 8 weeks after the transplantation (FIG. 5). The tumors contained foci with derivatives of endodermal, mesodermal and ectodermal embryonic germ layers: stratified cell epithelium (FIG. 5, panel 1), neuronal cells, cartilage, muscle (FIG. 5, panel 2), glandular structures (FIG. 5, panel 3) and endodermal high prismatic epithelium (FIG. 5, panel 3). Immunostaining was carried out with the germ layer markers cytokeratin for epithelial tissue in endoderm, TUJ-1 for neuroectodermal cells and a-fetoprotein (AFP) for endoderm. Alcian blue stained hyaline cartilage and epithelial glands.

In general, the generation of human adult GSCs from spermatogonial cells was reproducible: similar cell numbers were obtained from biopsies obtained from the 22 male patients (10 normal, 10 azoospermia, 2 sex reassignment surgeries) aged 17 to 81 years (data not shown). After selection the obtained yields of spermatogonial cells were age-dependent. Lesser amounts were generated from older people and patients with azoospermia. However, the doubling times of human adult GSC colonies were similar in all groups (data not shown). Human adult GSCs were successfully passaged for continuous undifferentiated proliferation in basic medium with LIF for up to 16 months and over more than 40 passages. The inventors did not observe a decline in the ability to form colony units between passages 3 and 36 (FIG. 2e). The colonies had a doubling time of 48 h. The undifferentiated human adult GSCs could be cryopreserved and thawed with no loss of proliferation or differentiation capacity. No replicative crisis was observed in any of the 22 different cell lines. Cytogenetic analysis showed that human adult GSCs had a normal karyotype (46 chromosomes, XY) in all examined metaphase spreads.

To determine whether human adult GSCs can differentiate in vitro, the inventors applied commonly used methods designed to induce differentiation of human ES cells into various cell lineages. On the whole, differentiated human adult GSCs displayed all morphological characteristics of the expected myogenic, osteogenic, pancreatic and neural lineages.

To analyze the differentiation capacity of human ES (H1) and human adult GSCs, the cells were differentiated into all specific lineages. The results were comparable, diverging only in the pancreatic lineage, where the inventors generated more insulin, glucagon- and c-peptide-positive cells from human adult GSCs.

To exclude possible contaminations during cell culturing, DNA microsatellite markers were analyzed in DNA preparations of all established cell cultures and compared with a marker profile of H1 embryonic stem cells. All cell cultures were analyzed after completion of all other experiments and showed independent genetic origins (data not shown), that is, each cell line is unique. Moreover, the inventors never observed more than two marker alleles, thus excluding relevant cell or DNA contamination for all cell lines.

REFERENCES 1. de Rooij, D. G. Rapid expansion of the spermatogonial stem cell tool box. *Proc. Natl Acad. Sci. USA* 103, 7939-7940 (2006).
2. Brinster, R. L. & Avarbock, M. R. Germline transmission of donor haplotype following spermatogonial transplantation. *Proc. Natl Acad. Sci. USA* 91, 11303-11307 (1994).
3. Kubota, H. & Brinster, R. L. Technology insight: In vitro culture of spermatogonial stem cells and their potential therapeutic uses. *Nature Clin. Pract. Endocrinol. Metab.* 2, 99-108 (2006).

4. Matsui, Y., Zsebo, K. & Hogan, B. L. Derivation of pluripotential embryonic stem cells from murine primordial germ cells in culture. *Cell* 70, 841-847 (1992).
5. Kanatsu-Shinohara, M. et al. Generation of pluripotent stem cells from neonatal mouse testis. *Cell* 119, 1001-1012 (2004).
6. Guan, K. et al. Pluripotency of spermatogonial stem cells from adult mouse testis. *Nature* 440, 1199-1203 (2006).
7. Stevens, L. C. Spontaneous and experimentally induced testicular teratomas in mice. *Cell Differ.* 15, 69-74 (1984).
8. Resnick, J. L., Bixler, L. S., Cheng, L. & Donovan, P. J. Long-term proliferation of mouse primordial germ cells in culture. *Nature* 359, 550-551 (1992).
9. Turnpenny, L. et al. Evaluating human embryonic germ cells: concord and conflict as pluripotent stem cells. *Stem Cells* 24, 212-220 (2006).
10. Seandel, M. et al. Generation of functional multipotent adult stem cells from GPR125+ germline progenitors. *Nature* 449, 346-350 (2007).
11. Meng, X. et al. Regulation of cell fate decision of undifferentiated spermatogonia by GDNF. *Science* 287, 1489-1493 (2000).
12. Kanatsu-Shinohara, M. et al. Leukemia inhibitory factor enhances formation of germ cell colonies in neonatal mouse testis culture. Biol. Reprod. 76, 55-62 (2007).
13. Shamblott, M. J. et al. Derivation of pluripotent stem cells from cultured human primordial germ cells. *Proc. Natl Acad. Sci. USA* 95, 13726-13731 (1998).
14. Shamblott, M. J. et al. Human embryonic germ cell derivatives express a broad range of developmentally distinct markers and proliferate extensively in vitro. *Proc. Natl Acad. Sci. USA* 98, 113-118 (2001).
15. Costoya, J. A. et al. Essential role of Plzf in maintenance of spermatogonial stem cells. *Nature Genet.* 36, 653-659 (2004).
16. Shinohara, T., Avarbock, M. R. & Brinster, R. L. $b_1$- and $a_6$-integrin are surface markers on mouse spermatogonial stem cells. *Proc. Natl Acad. Sci. USA* 96, 5504-5509 (1999).
17. Kubota, H., Avarbock, M. R. & Brinster, R. L. Culture conditions and single growth factors affect fate determination of mouse spermatogonial stem cells. *Biol. Reprod.* 71, 722-731 (2004).
18. Stukenborg, J. B. et al. Co-culture of spermatogonia with somatic cells in a novel three-dimensional soft-agar-culture-system. *J. Androl.* 29, 312-329 (2007).
19. Hamra, F. K. et al. Defining the spermatogonial stem cell. *Dev. Biol.* 269, 393-410 (2004).
20. Wernig, M. et al. In vitro reprogramming of fibroblasts into a pluripotent ES-cell-like state. *Nature* 448, 318-324 (2007).
21. Yu, J. et al. Induced pluripotent stem cell lines derived from human somatic cells. *Science* 318, 1917-1920 (2007).
22. Park, I. H. et al. Reprogramming of human somatic cells to pluripotency with defined factors. *Nature* 451, 141-146 (2008).
23. Meissner, A., Wernig, M. & Jaenisch, R. Direct reprogramming of genetically unmodified fibroblasts into pluripotent stem cells. *Nature Biotechnol.* 25, 1177-1181 (2007).
24. Okita, K., Ichisaka, T. & Yamanaka, S. Generation of germline-competent induced pluripotent stem cells. *Nature* 448, 313-317 (2007).
25. Ginis, I. et al. Differences between human and mouse embryonic stem cells. *Dev. Biol.* 269, 360-380 (2004).
26. Schatten, G., Smith, J., Navara, C., Park, J. H. & Pedersen, R. Culture of human embryonic stem cells. *Nature Methods* 2, 455-463 (2005).
27. Maltsev, V. A., Rohwedel, J., Hescheler, J. & Wobus, A. M. Embryonic stem cells differentiate in vitro into cardiomyocytes representing sinusnodal, atrial and ventricular cell types. *Mech. Dev.* 44, 41-50 (1993).
28. Kehat, I. et al. Development of cardiomyocytes from human ES cells. *Methods Enzymol.* 365, 461-473 (2003).
29. Ringe, J., Haupl, T. & Sittinger, M. Mesenchymal stem cells for tissue engineering of bone and cartilage. *Med. Klin.* 98 (suppl. 2), 35-40 (2003).
30. Bielby, R. C., Boccaccini, A. R., Polak, J. M. & Buttery, L. D. In vitro differentiation and in vivomineralization of osteogenic cells derived from human embryonic stem cells. *Tissue Eng.* 10, 1518-1525 (2004).
31. Lumelsky, N. et al. Differentiation of embryonic stem cells to insulin-secreting structures similar to pancreatic islets. *Science* 292, 1389-1394 (2001).
32. Segev, H., Fishman, B., Ziskind, A., Shulman, M. & Itskovitz-Eldor, J. Differentiation of human embryonic stem cells into insulin-producing clusters. *Stem Cells* 22, 265-274 (2004).
33. Blyszczuk, P. et al. Embryonic stem cells differentiate into insulin-producing cells without selection of nestin-expressing cells. *Int. J. Dev. Biol.* 48, 1095-1104 (2004).
34. Pollard, S. M., Conti, L., Sun, Y., Goffredo, D. & Smith, A. Adherent neural stem (NS) cells from fetal and adult forebrain. Cereb. *Cortex* 16 (suppl. 1), i112-i120 (2006).
35. Bibel, M. et al. Differentiation of mouse embryonic stem cells into a defined neuronal lineage. *Nature Neurosci.* 7, 1003-1009 (2004).
36. Wittwer, C. T., Fillmore, G. C. & Hillyard, D. R. Automated polymerase chain reaction in capillary tubes with hot air. *Nucleic Acids Res.* 17, 4353-4357 (1989).
37. Alexander, D. et al. Transcription factor Egr-1 activates collagen expression in immortalized fibroblasts or fibrosarcoma cells. *Biol. Chem.* 383, 1845-1853 (2002).

All before-identified references are incorporated herein by reference.

The invention claimed is:

1. A method for generating human adult pluripotent stem cells, comprising the following steps:
   (1) providing cells isolated from human testicular parenchyma,
   (2) cultivating said cells in the presence of glial cell-line derived neurotropic factor (GDNF),
   (3) isolating a first subpopulation of said cells expressing CD49f ($\alpha_6$ integrin),
   (4) contacting said first subpopulation with collagen,
   (5) isolating a second subpopulation from said first subpopulation consisting of cells not binding to said collagen ($Col_{NB}$ cells),
   (6) contacting said $Col_{NB}$ cells with laminin,
   (7) isolating a third subpopulation from said $Col_{NB}$ cells consisting of cells binding to said laminin ($Lam_B$ cells),
   (8) cultivating said $Lam_B$ cells in the presence of leukemia inhibitory factor (LIF) for obtaining human adult germ-line stem cells (GSCs) expressing VASA, CD49f and DAZL, wherein the GSCs are capable of forming teratomas in vivo after injection in immunodeficient mice characterized by foci with derivatives of endodermal, mesodermal and ectodermal embryonic germ layers expressing germ layer markers cytokeratin for epithelial tissue in endoderm, TUJ-1 for neuroectodermal cells and $\alpha$-fetoprotein (AFP) for endoderm.

2. The method of claim 1, wherein said isolation in step 3 is realized by performing magnetic activated cell separation (MACS) using beads comprising molecules capable of binding to CD49f ($\alpha_6$ integrin).

3. The method of claim 1, wherein step (8) comprises the following step:
   (8a) selection of cells with a normal karyotype (46, XY) to obtain said human adult GSCs.

4. The method of claim 1, wherein step (8) comprises the following step:
   (8b) selection of cells capable of inducing teratomas to obtain said human adult GSCs.

5. The method of claim 1, wherein step (8) comprises the following step:
(8c) selection of cells capable of differentiating into cells of all three germ layers to obtain said human adult GSCs.

6. The method of claim 1, wherein step (8) comprises the following step:
(8d) selection of cells with activated transcriptional regulatory network to obtain said human adult GSCs.

7. The method of claim 1, wherein in step (8) the cultivated cells were passaged approximately every 14 days.

8. The method of claim 1, wherein said cultivating in step (8) occurs in basic medium on a gelatin coated cell carrier.

9. The method of claim 1, wherein said cultivating in step (2) occurs in knockout medium on an uncoated cell carrier.

10. The method of claim 1, wherein said step (1) comprises the following steps:
(1a) mechanical disruption and/or enzymatic dissociation of human testicular parenchyma to obtain a digest, and
(1b) filtering said digest to obtain single cells isolated from said human testicular parenchyma.

\* \* \* \* \*